(12) United States Patent
Stegmiller et al.

(10) Patent No.: US 9,266,968 B2
(45) Date of Patent: Feb. 23, 2016

(54) PROCESS FOR OBTAINING CARBOXYMETHYL CELLULOSE FROM AGRO-INDUSTRIAL RESIDUES AND CARBOXYMETHYL CELLULOSE AND USE THEREOF

(71) Applicants: VALE S.A., Rio de Janeiro (BR); UNIVERSIDADE FEDERAL DO ESPIRITO SANTO, Vitória (BR)

(72) Inventors: Leonidio Stegmiller, Vitória (BR); Jose Antonino Alves e Silva Reis, Vitória (BR); Reinaldo Walmir De Jesus, Vitória (BR); Liliane Durans de Moraes Costa, São Luis (BR); Antonio Alberto Ribeiro Fernandes, Vitória (BR); Erica Dutra Albuquerque, Vitória (BR); Jeferson da Silva Correa, Boa Esperança Seropédica (BR); Mauricio Kuster Cunha, Vila Velha (BR); Marlon Christian Marianelli Bastos, Serra (BR); Patricia Machado Bueno Fernandes, Vitória (BR); Poliana Belisário Zorzal, Serra (BR)

(73) Assignees: VALE S.A., Rio de Janeiro (BR); UNIVERSIDADE FEDERAL DO ESPIRITO SANTO, Vitoriaes (BR)

( * ) Notice: Subject to any disclaimer, the term of this patent is extended or adjusted under 35 U.S.C. 154(b) by 124 days.

(21) Appl. No.: 13/890,996

(22) Filed: May 9, 2013

(65) Prior Publication Data

US 2013/0324711 A1 Dec. 5, 2013

Related U.S. Application Data

(60) Provisional application No. 61/644,856, filed on May 9, 2012.

(51) Int. Cl.
| | |
|---|---|
| C08B 11/12 | (2006.01) |
| A61K 31/717 | (2006.01) |
| C08B 11/02 | (2006.01) |
| C08B 1/06 | (2006.01) |
| C08H 8/00 | (2010.01) |
| C08L 1/28 | (2006.01) |
| D21C 5/00 | (2006.01) |
| D21C 9/00 | (2006.01) |
| D21H 11/12 | (2006.01) |
| D21H 11/16 | (2006.01) |
| D21H 11/20 | (2006.01) |
| D21H 17/20 | (2006.01) |
| D21H 17/26 | (2006.01) |

(Continued)

(52) U.S. Cl.
CPC ............... *C08B 11/02* (2013.01); *A23L 1/0534* (2013.01); *A61K 9/1652* (2013.01); *C08B 1/06* (2013.01); *C08B 11/12* (2013.01); *C08H 8/00* (2013.01); *C08L 1/286* (2013.01); *D21C 5/00* (2013.01); *D21C 9/002* (2013.01); *D21H 11/12* (2013.01); *D21H 11/16* (2013.01); *D21H 11/20* (2013.01); *D21H 17/20* (2013.01); *D21H 17/26* (2013.01)

(58) Field of Classification Search
CPC .......... C08B 11/02; C08B 1/06; C08B 11/12; C08H 8/00; C08L 1/286; D21C 5/00; D21C 9/002; A23L 1/0534; D21H 11/12; D21H 11/16; D21H 1/20; D21H 17/20; D21H 17/26; A61K 9/1652
USPC ............................................... 536/98; 514/57
See application file for complete search history.

(56) References Cited

U.S. PATENT DOCUMENTS

| | | | | |
|---|---|---|---|---|
| 2,054,301 A | * | 9/1936 | Richter | 162/187 |
| 2,650,881 A | * | 9/1953 | Forkner | 426/639 |

(Continued)

FOREIGN PATENT DOCUMENTS

| | | |
|---|---|---|
| CA | 1 247 306 | 12/1988 |
| CA | 1336641 | 8/1995 |
| GB | 730961 A1 * | 6/1995 |

OTHER PUBLICATIONS

Bondar et al.; SU 1669917 A1; Aug. 15, 1991 (Derwent English abstract).*
Abstract of E. I. Du Pont de Nemours; U.S. Pat. No. 6,512,688; Mar. 31, 1966 (abstract sent).*

*Primary Examiner* — Shaojia Anna Jiang
*Assistant Examiner* — Michael C Henry
(74) *Attorney, Agent, or Firm* — Arent Fox LLP (57) ABSTRACT

An advantageous and effective process for obtaining carboxymethyl cellulose (CMC) from agro-industrial residues, comprising the steps of a) Preparing the raw material, wherein the raw material is washed, dried, grounded and washed again; b) a pumping step, wherein the product obtained from the step a) is reacted with sodium hydroxide; c) a synthesis step, wherein consists in grounding the pulp; adding a solution of isopropanol and distilled water under stirring at room temperature; adding NaOH aqueous solution up to the alkalization of the mixture; adding monochloroacetic acid in isopropanol; filtrating; suspending in methanol solution and neutralizing with acetic acid. The CMC obtained from the process can be employed in a several industrial processes.

14 Claims, 7 Drawing Sheets

(51) Int. Cl.
*A61K 9/16* (2006.01)
*A23L 1/0534* (2006.01)

(56) References Cited

U.S. PATENT DOCUMENTS

| | | | |
|---|---|---|---|
| 3,678,031 A * | 7/1972 | Schoggen | 536/98 |
| 3,900,463 A | 8/1975 | Yada et al. | |
| 4,288,245 A | 9/1981 | Roorda et al. | |
| 4,401,813 A | 8/1983 | Lowell et al. | |
| 4,410,694 A | 10/1983 | Nakayama et al. | |
| 4,486,335 A | 12/1984 | Majewicz | |
| 4,597,797 A | 7/1986 | Roorda et al. | |
| 4,863,512 A | 9/1989 | Banyai et al. | |
| 4,919,711 A | 4/1990 | Banyai et al. | |
| 6,497,746 B1 | 12/2002 | Steeghs et al. | |
| 6,808,598 B1 * | 10/2004 | Takeuchi et al. | 162/115 |

* cited by examiner

(a) Pellets of iron ore using CMC-based Market Binder (b) Non-bleached Natural Fiber-Based Composition (c) Bleached Natural Fiber-Based Composition

PROCESS FOR OBTAINING CARBOXYMETHYL CELLULOSE FROM AGRO-INDUSTRIAL RESIDUES AND CARBOXYMETHYL CELLULOSE AND USE THEREOF

This application claims priority from U.S. Patent Application No. 61/644,856, titled "Natural fiber-based binder derived from agribusiness industry residues, and a process for obtaining a natural fiber-based binder," filed on May 9, 2012, and which is incorporated herein by reference in its entirety.

FIELD OF INVENTION

The present invention refers to a process for obtaining a fiber-based binder derived from agribusiness industry residues and carboxymethyl cellulose produced by the said process.

DESCRIPTION OF THE RELATED ART

Some binders produced with Sodium Carboxymethyl Cellulose (CMC) are known in the art. The documents below show examples of such binders and their corresponding production processes.

Brazilian Patent PI0801555-4 describes a binder for the pelletizing of iron ore. The binder in question contains bentonite and polysaccharide for use in the binding of finely ground iron ore. The invention also relates to a process for preparing pellets of iron ore wherein the composition comprising polysaccharide and bentonite is used with a binder.

U.S. Pat. No. 4,410,694 describes a process for the preparation of carboxymethyl cellulose fibers comprising continuously circulating a homogeneous alkaline reaction liquid through cellulose fibers packed in a reaction vessel, which cellulose fibers are selected from the group consisting of natural cellulose fibers and regenerated cellulose fibers, at a flow rate of said reaction liquid of greater than 10 l/min per Kg of said cellulose fibers, said reaction liquid comprising an effective amount of an etherifying agent selected from the group consisting of monochloroacetic acid and salts thereof, dissolved in a homogeneous alkaline solvent which consists essentially of ethanol and water, for a period of time sufficient to substantially completely convert said cellulose fibers into said carboxymethyl cellulose fibers.

U.S. Pat. No. 3,900,463 describes a process for preparing alkali carboxymethyl cellulose having a uniform distribution of the degree of substitution which comprises treating cellulose with an etherifying agent selected from the group consisting of alkali monochloroacetate and lower alkyl monochloroacetate in the presence of a solvent system consisting of at least one organic solvent and water until the uniform distribution of the etherifying agent into the cellulose is attained, the etherifying agent being used in 0.4 to 2.0 mol per cellulose glucose anhydride unit, and adding an alkali to the resultant mixture, the alkali being used in not less than an equimolar amount to alkali monochloroacetate or not less than a twice molar amount to lower alkyl monochloroacetate, followed by treatment at a temperature from room temperature to reflux temperature until the etherification is completed.

U.S. Pat. No. 4,401,813 describes a process for preparing a form of carboxymethyl cellulose which exhibits superior rheological and fluid loss characteristics in aqueous calcium chloride solutions which comprises conducting causticization of high molecular weight cellulose in the absence of oxygen, at a temperature less than 350° C., in an aqueous solution containing 86.9±2% by weight isopropanol, at an isopropanol-water solution to cellulose weight ratio from 2 to 1 to 7.5 to 1, and in the presence of sufficient alkali metal hydroxide such that the alkali metal hydroxide to monochloroacetic acid molar ratio during the subsequent etherification of the alkali cellulose is greater than 2.00 to 1, wherein the monochloroacetic acid utilized contains less than about 2% by weight dichloroacetic acid.

The CMC used in the mining industry, more particularly as a binder ore is responsible by the agglomeration of ore particles. The pellets formation is one of the most important stages of pelletizing process, being influenced by several factors, with direct outcomes on the final product quality.

CA 1,336,641 describes a binder for iron ore in the presence of water, containing 10% to 90% of Sodium Carboxymethyl Cellulose soluble in water and 10% to 90% of sodium carbonate. The patent also describes the process for the use of binder in the ore.

CA 1,247,306 describes a process for binding of iron ore particles using a binder consisting of hydroxyethyl cellulose and sodium carbonate in the presence of water.

U.S. Pat. No. 4,288,245 describes a process for the pelletizing of metallic ores in the presence of a paste containing alkali metal salt and carboxymethyl cellulose in an amount of at least 0.01%, in combination with one or more salts derived from an alkali metal and an acid.

U.S. Pat. No. 4,486,335 describes a process for the production of binders of ore containing iron and the product of the process. The invention describes a carboxymethyl hydroxyethyl cellulose-based binder, which, when bonded to an aluminum ion in an aqueous solution, forms a gel.

U.S. Pat. No. 4,597,797 describes a binder for ores in the presence of water and an alkali metal salt of carboxymethyl cellulose as a binder. The composition comprises an alkali metal salt of carboxymethyl cellulose and one or more salts derived from an alkali metal and a weak acid. The alkali salts of weak acids are preferably those derived from acetic acid, benzoic acid, lactic acid, propionic acid, tartaric acid, succinic acid, citric acid, nitrous acid, boric acid and carbonic acid.

U.S. Pat. No. 4,863,512 refers to a useful binder for binding concentrated ore material in the presence of water comprising an alkali metal salt of carboxymethyl cellulose and sodium tripolyphosphate, a process for binding concentrated ore material with such paste, and the bound product resulting from such process.

U.S. Pat. No. 4,919,711 discloses a useful binder for binding a concentrated ore material in the presence of water comprising a selected water soluble polymer, consisting of alkali metal salts of carboxymethyl cellulose or carboxymethyl hydroxyethyl cellulose and sodium tripolyphosphate. In addition to the product, the patent describes a process for binding concentrated ore material with such paste, and the bound product resulting from such process.

U.S. Pat. No. 6,497,746 describes a process for binding particles (e.g. pelletizing) and the product produced (i.e., pellets) by such a process. It is a process for binding particulate material, comprising an effective amount of water for wetting, an effective amount of binding of a polymer selected as starch, modified starch, starch derivatives, alginates, pectins and mixtures thereof and an effective amount of binding of the salt of a weak acid to produce a mixture.

Brazil is one of the largest generators of agro-industrial waste. These wastes are released into the environment without any previous treatment can cause several damages.

As agro-industrial fiber residues, the coconut stands out in this scenario to be produced on a large scale. It is estimated that the annual production of coconut in Brazil is more than 1.5 billion units, harvested from an area of over 280,000 hectares. The processing of coconut generating activity is a waste after withdrawing the solid albumen of interest for obtaining coconut water and coconut, remaining parts represented by fibrous epicarp, mesocarp and endocarp, which constitute about 45% of the components of the fruit. Such residues are difficult to discard, being sent to dumps and landfills, and raise industry costs with transportation to these locations.

Face to the aforementioned problems, the present invention refers to a sustainable alternative to obtain carboxymethyl cellulose by using agro-industrial waste.

The huge amount of waste aforementioned of nearly two million tons of coconut fiber mesocarp through the process proposed by the present invention can be used as the raw material for the production of carboxymethyl cellulose.

SUMMARY OF THE INVENTION

In light of the above described problems and unmet needs, the present invention describes an advantageous and effective process for obtaining carboxymethyl cellulose (CMC) from agro-industrial residues, comprising the steps of a) Preparing the raw material, wherein the raw material is washed, dried, grounded and washed again; b) a pumping step, wherein the product obtained from the step a) is reacted with sodium hydroxide; c) a synthesis step, wherein consists in grounding the pulp; adding a solution of isopropanol and distilled water under stirring at room temperature; adding NaOH aqueous solution up to the alkalization of the mixture; adding monochloroacetic acid in isopropanol; filtrating; suspending in methanol solution and neutralizing with acetic acid.

The present invention also relates to the CMC obtained from the said process which can be employed in a several industrial processes.

Additional advantages and novel features of these aspects of the invention will be set forth in part in the description that follows, and in part will become more apparent to those skilled in the art upon examination of the following or upon learning by practice of the invention.

BRIEF DESCRIPTION OF THE DRAWINGS

Various example aspects of the systems and methods will be described in detail, with reference to the following Fig. but not limited to, wherein:

FIG. 1 is a Scanning Microscopy of CMC-based market binder.

FIG. 2 is a Scanning Microscopy of the market pure CMC.

FIG. 3 is a Scanning Microscopy of the CMC from the process of the present invention without bleaching stage.

FIG. 4 is a Scanning Microscopy of the CMC from the process of the present invention with bleaching stage.

FIG. 5 is an Infrared spectrum of the bleached pulp.

FIG. 6 is an Infrared Spectrum of CMC obtained from coconut fiber.

FIG. 7 is an Infrared Spectrum of Market Pure CMC.

FIG. 8 is an Infrared Spectrum of CMC-based Market Binder.

FIG. 9 shows Pellets of iron ore using (a) CMC-based Market Binder, (b) non-bleached natural fiber-based composition and (c) bleached natural fiber-based composition.

DETAILED DESCRIPTION OF THE INVENTION

The following detailed description does not intend to, in any way, limit the scope, applicability or configuration of the invention. More exactly, the following description provides the necessary understanding for implementing the exemplary modalities. When using the teachings provided herein, those skilled in the art will recognize suitable alternatives that can be used, without extrapolating the scope of the present invention.

The present invention relates to a process for obtaining a natural CMC component derived from agribusiness residues, and more particularly to a process for obtaining a natural CMC derived from coconut fiber.

More specifically, the present invention describes a process for obtaining a natural CMC component, which comprises the following steps:

a) Preparing the raw material;
b) Pulping step;
c) Synthesis of CMC.

In the step a) the agro-industrial fiber residues, as coconut fiber, are washed with water to remove gross impurities. After such washing, the fiber is dried in an oven at 30-120° C., for 4-72 hours.

The fiber is ground in a mill and sieved through a sieve of 18 to 140 mesh (1.00 to 0.105 mm).

After being grounded, the product is washed with distilled water and then filtrated. The precipitate is then dried in an oven at 30-120° C., for 4-72 hours.

In order to remove the lignin from the product obtained, in the step b) (pulping step) the mass of grounded and cleaned fiber obtained in the step a) is mixed and stirring reacted with sodium hydroxide 5-25% (m/v), in the ratio of 1:10 during 10-100 minutes.

Optionally, after stirring the reaction mixture it can be subjected to pressure of 0.5-3.0 Kgf/cm$^2$, for 10-100 minutes, in a temperature of 111 to 143° C.

The reaction mixture is washed with water in a neutral pH and the precipitate is taken to an oven for about 12-18 hours at 30-120° C.

The product obtained from the step b) is carried out by means of controlled stirring and temperature for the synthesis (step c)) of CMC. Initially, the dried pulp is grounded, then a solution of isopropanol (1:15-1:30) and distilled water (1:0.5-1:3) is added. The system is kept under stirring at room temperature for 10-30 minutes. After that, NaOH aqueous solution is added at 25-55% (w/v) is added, in a ratio of 1:15 of dried pulp. A solution of sodium hydroxide is added dropwise during 30 minutes under stirring at room temperature and after the addition the mixture is kept under stirring for 60 minutes at room temperature.

Soon after the alkalization of the cellulose, a solution consisting of monochloroacetic acid (1:1.5-1:3.5) in isopropanol (1:1-1:5) is added. Such solution is added dropwise during 10-40 minutes, under stirring at room temperature. Then, the temperature is raised to 40-70° C., and the reaction is allowed to proceed for 2-5 hours.

After the synthesis, the product is filtrated, then suspended in 70-90% of methanol solution (v/v), neutralized with acetic acid and stirred for 5-20 minutes. It is filtered and washed twice with 60-90% of methanol, twice with P.A. methanol and finally CMC is dried.

Optionally, after the pulping step b), the material can be subjected to a bleaching. The decision of carrying out this step or not refers to the final result: the final material can be bleached or not.

The crude pulp obtained from the pulping step b) with distilled water (in the ratio 1:40) is stirred and maintained in a temperature of 60° C. After thermal equilibrium is achieved, glacial acetic acid (1:0.125 to 1:1) and sodium chlorite (1:0.5 to 1:4) are added. The reaction mixture is maintained under constant stirring for 0.5 to 1.5 hour and then cooled in an ice-bath below 10° C. Then the mixture is filtered until the filtrate became colorless, with neutral pH. Afterwards, a separation is carried out in a solution of sodium hydroxide 0.1 mol/L under stirring at room temperature for 90 minutes. Then the pulp is filtered again and washed with distilled water until the filtrate achieved a neutral pH.

With the process for obtaining carboxymethyl cellulose according to the present invention it is possible to remove about 80% of lignin from the agro-industrial using an alkaline treatment (pulping) softer than the known technique, representing savings in the initial process.

Furthermore, with an optional chemical bleaching step of the process of the present invention it is possible to achieve 95-100% of removal of polyphenols, and during the process it became clear that the control as to the reaction time and use of reflux is crucial for obtaining a quality product.

The natural CMC obtained can be used in a several industrial processes. The obtained natural CMC can be used as a natural fiber-based binder, in the mining industries, said natural fiber-based binder comprising a mixture of ingredients, which generates the advantages of the binding of the final product.

For example, for binding ore particles, the binder composition can vary due to kind, source and ore constitution.

These ingredients can be:
CMC from agro-industrial fiber residues 40-65%;
Sodium carbonate 15-40%;
Sodium chlorite 5-30%;
Others 0-20%—as sodium citrate, sodium glucolate and sodium hydroxide. The sodium hydroxide also can be used in the activation and in the efficiency increase in pelletizing process.

The mixture of these ingredients can be realized as a solid-solid mixture or a solid-liquid dispersion, in both cases the CMC is solid fraction and the additives may be solid or liquid.

Used as binder ore, the natural fiber-based composition derived from agro-industrial fiber residues is responsible by the agglomeration of ore particles. The pellets formation is one of the most important stages of pelletizing process, being influenced by several factors, with direct outcomes on the final product quality. The natural fiber-based composition quality is one of the most important requisites on pellets formation, ensuring suitable properties.

Furthermore, the CMC obtained by the process described herein can be used in the food industry as a viscosity modifier or thickener, and to stabilize emulsions in various products including ice cream. It is also a constituent of many non-food products, such as personal lubricants, toothpaste, laxatives, diet pills, water-based paints, detergents, textile sizing, and various paper products. It is used primarily because it has high viscosity, is nontoxic, and is hypoallergenic.

Example 1

Morphological Analysis

For analyzing the structure of the fiber after treatment proposed by the present invention is performed using the morphological analysis scanning electron microscopy (SEM).

The CMC-based market binder, the market pure CMC, and CMC from the process of the present invention are compared by SEM.

Figure 01:
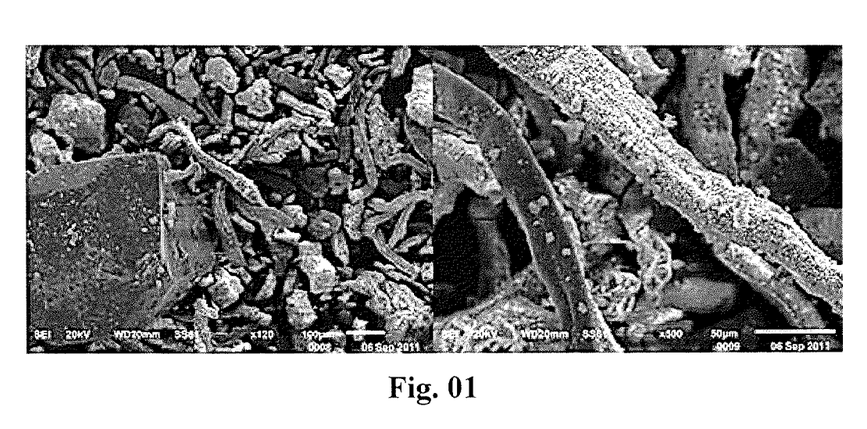
Figure 02:
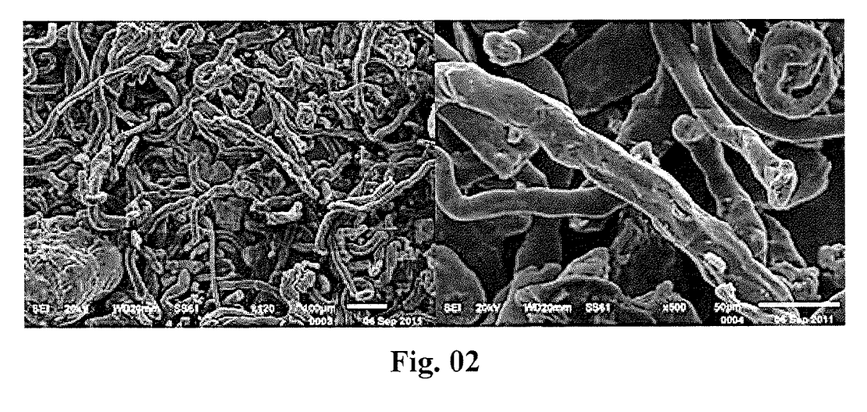

The morphological analysis in SEM showed that the CMC-based market binder contained $Na_2CO_3$ (FIG. 1). Additionally, the U.S. Pat. No. 4,948,430 also describes a carboxymethyl cellulose-based binder containing $Na_2CO_3$ in its composition and the process for application of such binder. However, sodium salts are not present in the market pure CMC (FIG. 2).

Figure 03:
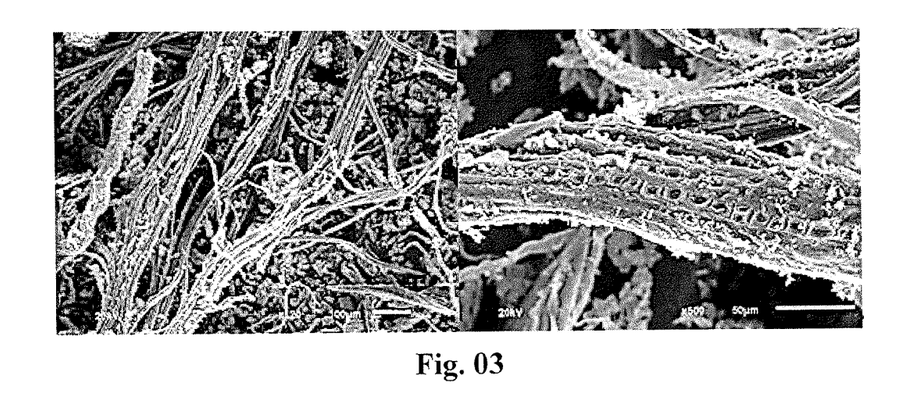
Figure 04:
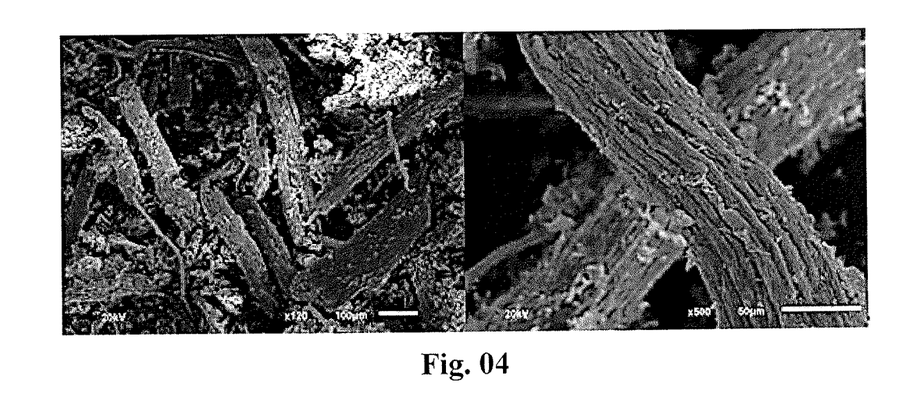

FIG. 3 and FIG. 4 show the SEM images of the product obtained from the process of the present invention. FIG. 3 presents the microscopic picture of the CMC obtained from coconut fiber without bleaching stage and FIG. 4 shows the image of the CMC obtained from coconut fiber with the bleaching stage, demonstrating that the fiber structure obtained resembles the fibers found in commercial products.

Example 2

Infrared Analysis

The main purpose of the infrared analysis (IR) is to confirm whether there was actually an etherification reaction and through the attributions of the corresponding bands of each vibration of the molecule.

The infrared analysis was carried out in samples of the bleached pulp, CMC obtained from coconut fiber, Market Pure CMC and CMC-based Market Binder.

Figure 05:
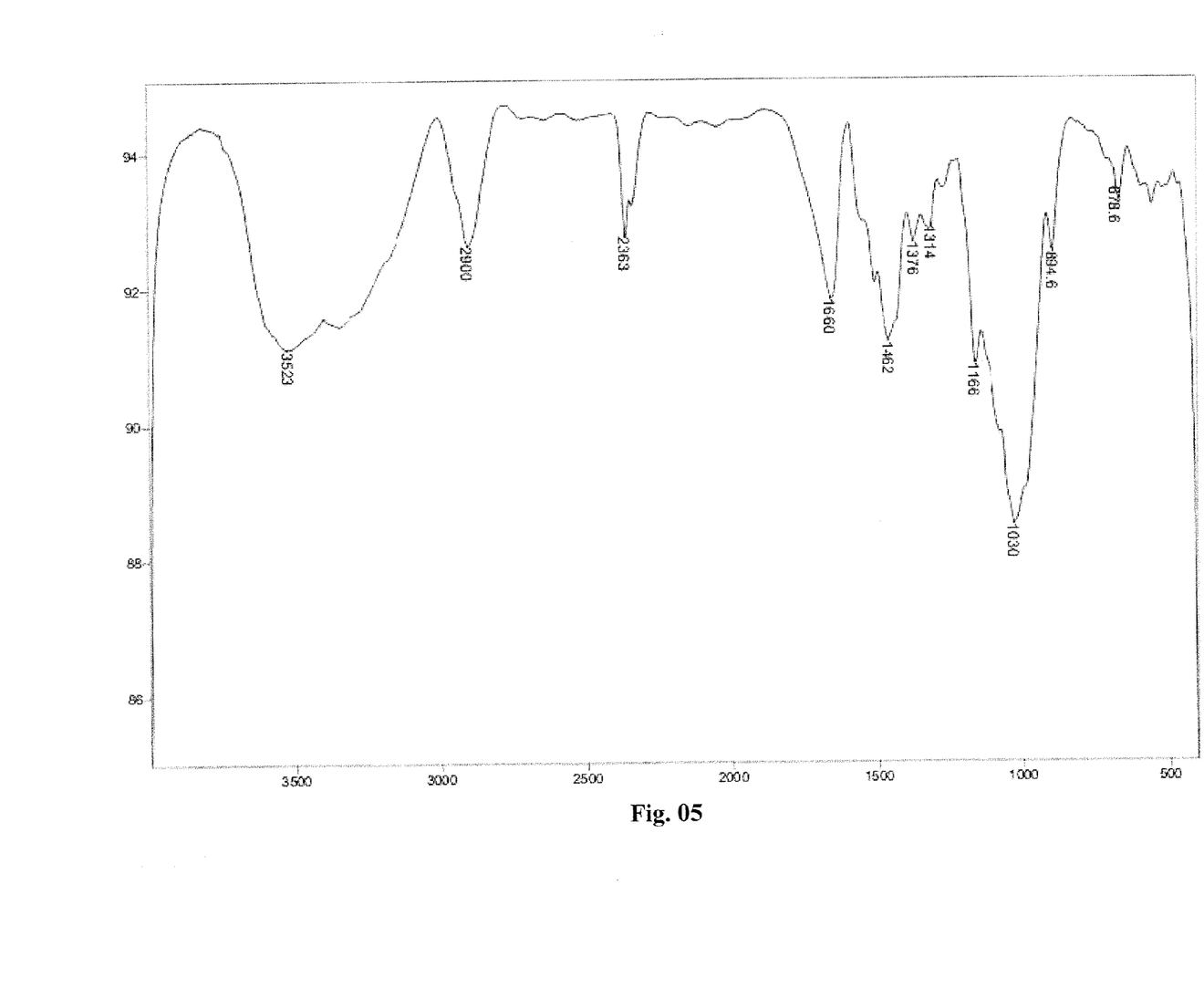

The purpose of the IR analysis for the bleached pulp (FIG. 5) is to confirm the chemical structure of cellulose. The infrared spectrum showed the following bands of the following functional groups O—H group (band around $3500\ cm^{-1}$) and Alkyl groups (band around $2900\ cm^{-1}$).

Figure 06:
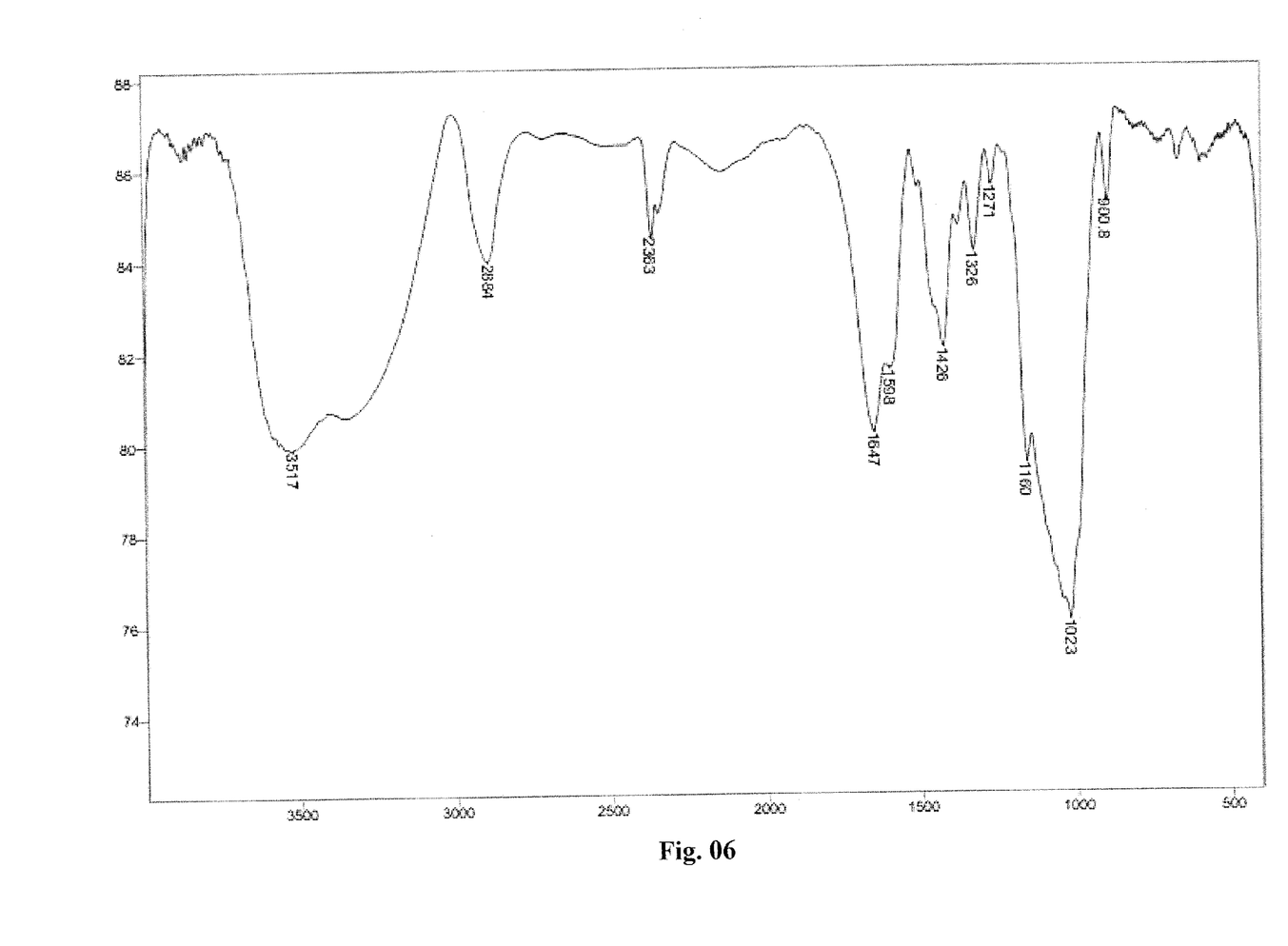
Figure 07:
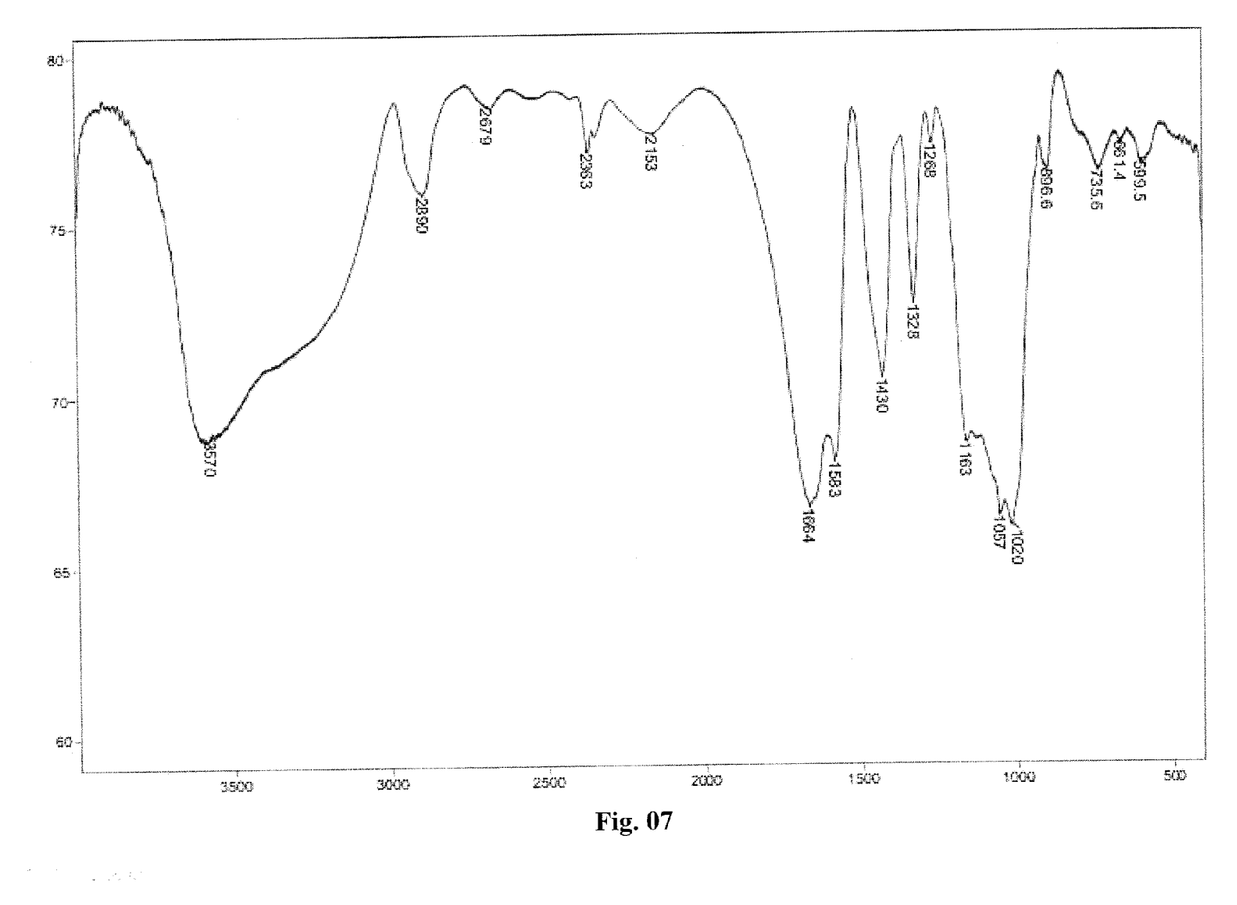

Comparing the CMC spectrum obtained from the coconut fiber (FIG. 6) with the market pure CMC (FIG. 7), we observed a similarity in the peaks of axial deformation of the carbonyl (C—O) having a similar frequency in 1647-1664 $cm^{-1}$ corresponding to the vibration of axial deformation of carbonyl of sodium carboxylate. All infrared spectra show similar features, but there is a displacement of the bands in the sample produced from coconut fibers, such fact can be explained by the production of other compounds in the obtaining or due to the degradation of cellulose.

Figure 08:
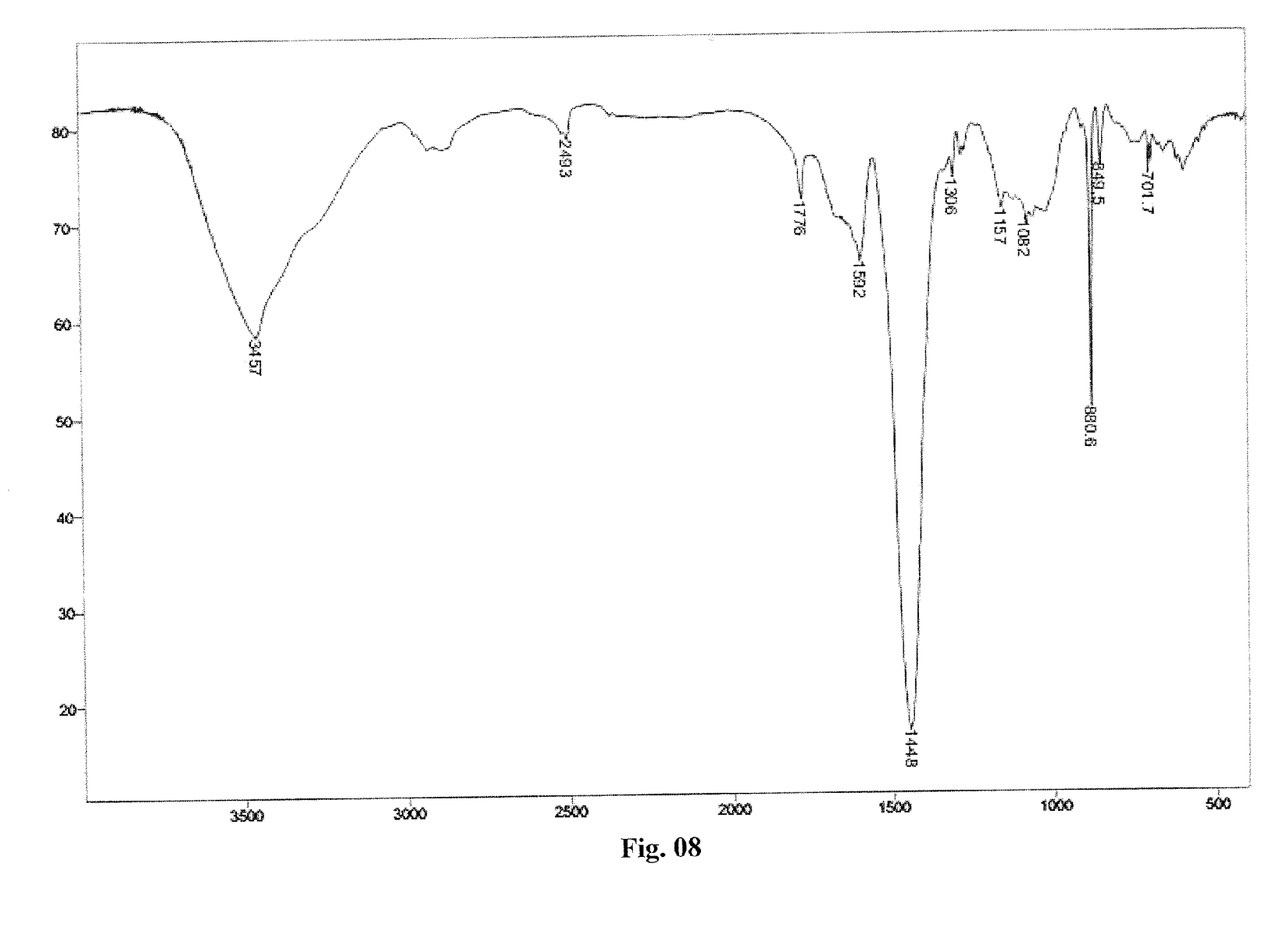

When comparing CMC obtained from coconut fiber and market pure CMC and CMC-based market binder (FIG. 8), we may observe some differences in the infrared spectrum. A notable difference is the more intense presence of bands in 1770 $cm^{-1}$ and in the absence of bands in the absorption frequency in 1660-1640 $cm^{-1}$, such displacement of the bands is due to the fact that a proportion of $Na_2CO_3$ is added to CMC, the former, in its turn, may result in more acidic features to CMC, so the carboxymethyl group may be expressed in larger amounts in the form of carboxylic acid and carboxylate ester. Another peak appearing in the infrared spectrum of CMC-based market binder, differing from the others, is the presence of an intense peak in 1448 $cm^{-1}$ which may be due to a C—O deformation of the carbonate carbonyl.

Example 3

Iron Ore Pelletizing Using CMC from Coconut Fiber

As previously indicated, the present invention proved useful in the agglomeration of iron ore particles. To complement the studies, tests were carried out to prove the efficacy of the invention.

Figure 09:
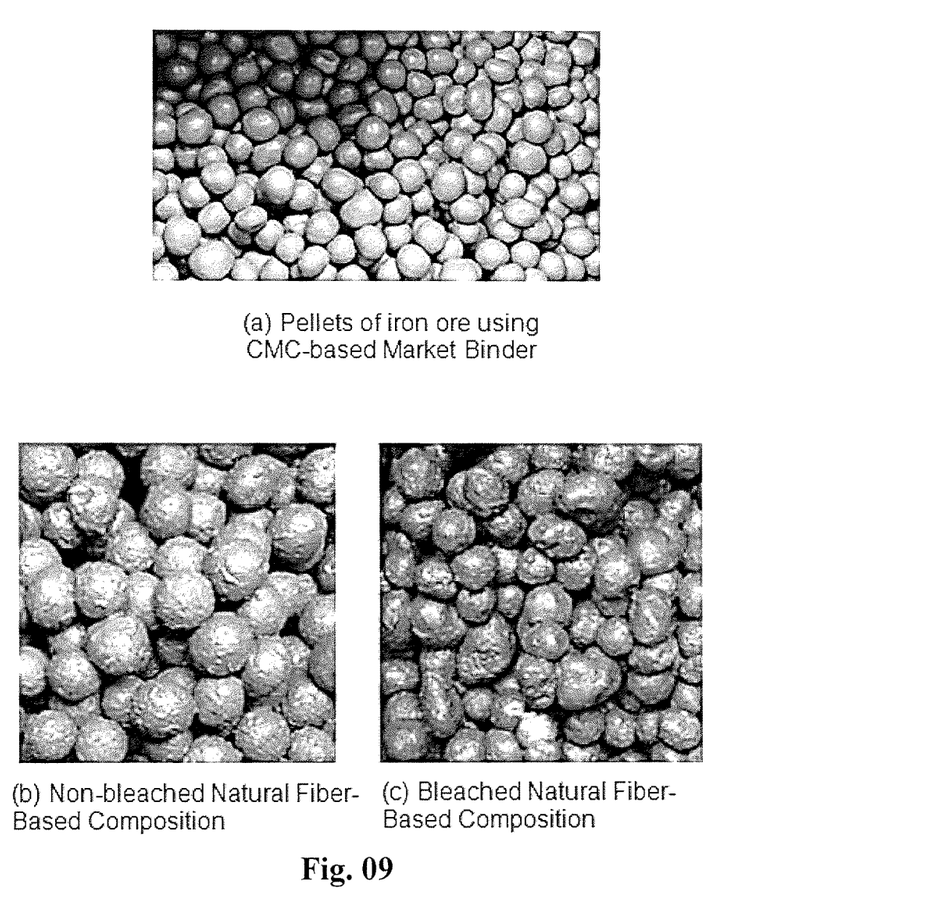

Tests of pelletizing and burn pot grate pelletizing plant with satisfactory results showed on FIG. 9.

Tests were conducted addressing the use of CMC bleaching stage with and without the bleaching stage, in comparison with CMC-based Market Binder as shown on Table 1.

Finally, it should be understood that the FIGS. show exemplificative embodiments of the present invention, with the real scope of the invention object being defined only in the enclosed claims.

TABLE 1

| | | Development of natural fiber-based binder from agro-industrial fiber residues | | |
|---|---|---|---|---|
| Results of physical tests | | CMC-based Market Binder | CMC bleaching stage with | CMC without the bleaching stage |
| Indurated Pellet | Abrasion Index (%) | 4.9 | 4.9 | 5.1 |
| | Compression Strength (daN/pel.) | 327 | 332 | 275 |
| | Cracks Nunber | 12 | 15 | 38 |
| Green Pellet | Moisture (%) | 9.0 | 9.0 | 9.0 |
| | Dry Compression Strength (kg/pel.) | 2.4 | 1.4 | 0.82 |
| | Wet Compression Strength (kg/pel.) | 1.4 | 1.1 | 1.03 |
| | Drop Number (45 cm) | 4.5 | 3.1 | 3.60 |

The invention claimed is:

1. A process for obtaining carboxymethyl cellulose from agro-industrial residues, comprising:
   a) preparing a raw material comprising coconut fiber, wherein the raw material is washed, dried, ground, and sieved for particles of about 0.105 mm to about 1.00 mm or less, wherein the particles are washed;
   b) pulping, wherein the product obtained from step a) is reacted with sodium hydroxide to form a reaction mixture and the reaction mixture is stirred;
   c) synthesis, comprising:
      grinding the reaction mixture obtained from step b);
      adding a solution of isopropanol and distilled water under stirring at room temperature;
      adding NaOH aqueous solution up to alkalization of the mixture;
      adding monochloroacetic acid in isopropanol;
      filtrating;
      suspending in methanol solution; and
      neutralizing with acetic acid.

2. The process according to claim 1, where step a) comprises drying in an oven at 30-120° C., for 4-72 hours; and sieving through a sieve of 18 to 140 mesh.

3. The process according to claim 1, wherein the sodium hydroxide in step b) comprises a concentration of 5-25% (m/v), and is in a ratio of 1:10, and wherein the pulping step has a duration of 10-100 minutes.

4. The process according to claim 1, wherein after stirring the reaction mixture in step b), subjecting the reaction mixture to a pressure of 0.5-3.0 Kgf/cm$^2$, for 10-100 minutes, at a temperature of 111 to 143° C.

5. The process according to claim 1, wherein the solution of isopropanol is at a concentration of 1:15-1:30; distillated water is added; the NaOH aqueous solution added is at a concentration of 25-55% (w/v), in a ratio of 1:15 of dried pulp; the solution of monochloroacetic acid is at a concentration of 1:1.5-1:3.5 in isopropanol 1:1-1:5.

6. The process according to claim 1, wherein after the pulping step b), the material is subjected to a bleaching step.

7. The process according to claim 1, wherein the coconut fiber is mesocarp fiber.

8. A process for obtaining a binder composition for the production of ore pellets, comprising:
   obtaining carboxymethyl cellulose obtained by the process as defined in claim 1; and
   combining the carboxymethyl cellulose with one or more components selected from a group consisting of sodium carbonate, sodium chlorite, sodium citrate and sodium glucolate.

9. The process according to claim 8, wherein the combining the carboxymethyl cellulose with one or more components comprises combining the carboxymethyl cellulose with 15-40% by weight sodium carbonate and 5-30% by weight sodium chlorite.

10. A process for obtaining a food product, comprising:
    obtaining carboxymethyl cellulose according to the process as defined in claim 1; and
    using the carboxymethyl cellulose as an additive in the food product.

11. A process for obtaining a pharmaceutical product, comprising:
    obtaining carboxymethyl cellulose according to the process as defined in claim 1; and
    using the carboxymethyl cellulose as an additive in the pharmaceutical product.

12. A process for obtaining a paper product, comprising:
    obtaining carboxymethyl cellulose according to the process as defined in claim 1; and
    using the carboxymethyl cellulose as an additive in the paper product.

13. A process for obtaining a textile product, comprising:
    obtaining carboxymethyl cellulose according to the process as defined in claim 1; and
    using the carboxymethyl cellulose as an additive in the textile product.

14. A binder composition, suitable for binding ore particles, comprising:
    40 to 65% by weight carboxymethyl cellulose obtained by the process as defined in claims 1;
    15 to 40% by weight sodium carbonate;
    5 to 30% by weight sodium chlorite; and
    0 to 20% by weight of one or more component selected from a group consisting of sodium citrate, sodium glucolate and sodium hydroxide.

* * * * *